(12) United States Patent
Zhao

(10) Patent No.: US 11,497,385 B2
(45) Date of Patent: Nov. 15, 2022

(54) REVERSAL SYSTEM FOR AN ENDOSCOPE AND AN ENDOSCOPE

(71) Applicant: OLYMPUS WINTER & IBE GMBH, Hamburg (DE)

(72) Inventor: Jianxin Zhao, Hamburg (DE)

(73) Assignee: OLYMPUS WINTER & IBE GMBH, Hamburg (DE)

(*) Notice: Subject to any disclaimer, the term of this patent is extended or adjusted under 35 U.S.C. 154(b) by 68 days.

(21) Appl. No.: 16/879,834

(22) Filed: May 21, 2020

(65) Prior Publication Data

US 2020/0383556 A1    Dec. 10, 2020

(30) Foreign Application Priority Data

Jun. 6, 2019  (DE) .......................... 102019115302.6

(51) Int. Cl.
| A61B 1/00 | (2006.01) |
| A61B 1/04 | (2006.01) |
| A61B 1/313 | (2006.01) |

(52) U.S. Cl.
CPC ...... *A61B 1/00195* (2013.01); *A61B 1/00009* (2013.01); *A61B 1/00147* (2013.01); *A61B 1/04* (2013.01); *A61B 1/313* (2013.01)

(58) Field of Classification Search
None
See application file for complete search history.

(56) References Cited

U.S. PATENT DOCUMENTS

| 3,442,573 | A | * | 5/1969 | Karl | ............... | G02B 15/145125 |
| | | | | | | 359/684 |
| 4,779,967 | A | * | 10/1988 | Murphy | ................. | G02B 21/02 |
| | | | | | | 359/379 |
| 4,988,172 | A | * | 1/1991 | Kanamori | .......... | G02B 23/2446 |
| | | | | | | 359/654 |
| 5,457,576 | A | * | 10/1995 | Atkinson | ............... | A61B 1/002 |
| | | | | | | 359/435 |

(Continued)

FOREIGN PATENT DOCUMENTS

| DE | 112004002220 B4 | 4/2008 |
| DE | 102012200146 A1 | 7/2013 |

(Continued)

OTHER PUBLICATIONS

WO2017199613 Ushi Yasuaki Nov. 23, 2017.*

(Continued)

*Primary Examiner* — John P Leubecker
*Assistant Examiner* — Minqiao Huang
(74) *Attorney, Agent, or Firm* — Scully, Scott, Murphy & Presser, P.C.

(57) ABSTRACT

A reversal system for an endoscope, the reversal system including: first and second outer achromats each comprising at least two lenses, wherein the first and second outer achromats have an outer diameter; first and second inner achromats arranged between the first and second outer achromats, wherein each of the first and second inner achromats comprises at least two lenses; and a holding sleeve for accommodating the at least two lenses of one or more of the first and second inner achromats, wherein the holding sleeve with the at least one of the first and second inner achromats is arranged between the first and second outer achromats.

10 Claims, 2 Drawing Sheets

(56) References Cited

U.S. PATENT DOCUMENTS

| | | | | |
|---|---|---|---|---|
| 5,891,015 A * | 4/1999 | Strahle | A61B 1/055 | 600/160 |
| 5,892,625 A * | 4/1999 | Heimer | A61B 1/002 | 359/665 |
| 6,341,876 B1 * | 1/2002 | Moss | G02B 6/0006 | 362/243 |
| 6,490,085 B1 * | 12/2002 | Zobel | G02B 23/2446 | 359/435 |
| 7,630,148 B1 * | 12/2009 | Yang | G02B 23/2484 | 359/740 |
| 10,054,772 B1 * | 8/2018 | Zobel | G02B 23/243 | |
| 2005/0143626 A1 * | 6/2005 | Prescott | A61B 1/00195 | 600/162 |
| 2006/0041193 A1 * | 2/2006 | Wright | A61B 1/042 | 600/179 |
| 2010/0254031 A1 * | 10/2010 | Roos | G02B 6/4296 | 359/820 |
| 2013/0194667 A1 * | 8/2013 | Inoue | G02B 27/0056 | 359/558 |
| 2014/0235947 A1 * | 8/2014 | Dahmen | A61B 1/00142 | 600/129 |
| 2014/0313578 A1 * | 10/2014 | Schouwink | G02B 27/0025 | 359/434 |
| 2014/0320621 A1 * | 10/2014 | Sonnenschein | A61B 1/0055 | 348/76 |
| 2014/0357951 A1 * | 12/2014 | Muller | A61B 1/06 | 600/111 |
| 2015/0085355 A1 * | 3/2015 | Krattiger | G02C 7/081 | 359/368 |
| 2015/0099983 A1 * | 4/2015 | Hatzilias | A61B 5/1077 | 600/478 |
| 2016/0170167 A1 * | 6/2016 | Takama | H04N 5/2254 | 348/335 |
| 2016/0370529 A1 * | 12/2016 | Angelini | G02B 6/0006 | |
| 2017/0035275 A1 * | 2/2017 | Yajima | A61B 1/07 | |
| 2017/0293139 A1 * | 10/2017 | Rehe | A61B 1/00188 | |
| 2018/0360297 A1 * | 12/2018 | Khettal | A61B 1/00193 | |
| 2018/0364473 A1 * | 12/2018 | Khettal | A61B 1/00193 | |
| 2019/0000308 A1 * | 1/2019 | Duckett, III | A61B 1/00133 | |
| 2019/0121116 A1 * | 4/2019 | Amanai | G02B 13/0095 | |

FOREIGN PATENT DOCUMENTS

| | | |
|---|---|---|
| DE | 10 2012 105 727 A1 | 1/2014 |
| DE | 10 2013 101 650 A1 | 8/2014 |
| JP | 2007-522507 A | 8/2007 |
| JP | 2017-203935 A | 11/2017 |
| WO | WO 95/35522 A1 | 6/1995 |
| WO | 2017/199613 A1 | 11/2017 |
| WO | 2018/123583 A1 | 7/2018 |
| WO | 2018/135192 A1 | 7/2018 |
| WO | 2018/186100 A1 | 10/2018 |

OTHER PUBLICATIONS

English abstract only of WO 2005/081033 A1.
Japanese Office Action dated Jan. 1, 2022 received in 2020-097904.

* cited by examiner

REVERSAL SYSTEM FOR AN ENDOSCOPE AND AN ENDOSCOPE

CROSS-REFERENCE TO RELATED APPLICATION

The present application claims the benefit to DE 10 2019 115 302.6 filed on Jun. 6, 2019, the entire contents of which is incorporated herein by reference.

FIELD

The present disclosure relates to a reversal system for an endoscope, in particular a laparoscope or uroscope, as well as an endoscope, in particular a laparoscope or uroscope.

PRIOR ART

As is known in the prior art, rigid endoscopes normally have an optical system which consists of an objective, an eyepiece and a relay lens system arranged therebetween, wherein the relay lens system has several reversal systems. Normally, an uneven number of reversal systems is provided since the objective and each reversal system generates a reversed image, and a normal endoscope should generate an upright image, whereby the generated image is orientated upright. In order to correct significant imaging errors, a symmetrical design of reversal systems is provided.

For example, a reversal system for an optical system of a rigid endoscope is known from DE 11 2004 002 220 B4. Furthermore, DE 10 2012 200 146 A1 describes a reversal system for an endoscope with a plurality of equivalent reversal systems.

It is further known that reversal systems are used in laparoscopes. Preferably in this context so-called short reversal systems are used. The short reversal systems contain two symmetrical lens groups consisting of two achromats which are mounted together in a system tube, wherein spacers are arranged between the achromats of the two lens groups. It has been revealed that the short reversal systems have a particularly unstable design in laparoscopes.

SUMMARY

An object is providing reversal systems for endoscopes, as well as an endoscope with corresponding reversal systems in which optical performance is easily improved.

Such objective can be achieved by a reversal system for an endoscope, such as, a laparoscope or uroscope, with two outer achromats each having at least two lenses, wherein the outer achromats have an outer diameter, and with two inner achromats arranged between the outer achromats, wherein each of the inner achromats has at least two lenses, wherein the lenses of an inner achromat, or the lenses of the inner achromats, are accommodated in a holding sleeve, wherein the holding sleeve with an inner achromat, or with the two inner achromats, is arranged between the outer achromats.

A tilting of the inner achromats, which are arranged between the two outer achromats, is reduced or avoided by arranging at least one inner achromat, or the two inner achromats, in the holding sleeve. Since at least one or the two inner achromats are securely positioned and aligned in the holding sleeve, the inner achromats are easily arranged, for example using a centering device, in the holding sleeve configured as a frame for the inner achromats.

The outer diameters of the inner achromats can be smaller than the outer diameters of one or the two outer achromats.

The outer achromats can be arranged adjacent to, or opposite the ends of, the holding sleeve. It is moreover provided that the outer achromats and the holding sleeve with one or the two inner achromats can be surrounded by a system tube of an endoscope, such as a fiber tube, or by a common holder, or are respectively arranged therein adjacent to each other, or respectively sequentially relative to the optical axis of the endoscope.

The outer achromats as well as the inner achromats can be configured as glued or cemented doublet achromats or triplet achromats.

Overall, an optical system of an endoscope can be improved by the reversal system since the optical performance is enhanced.

The inner achromats can each have an outer diameter, wherein the outer diameter of an inner achromat, or the outer diameter of the inner achromats, is smaller than the outer diameter of the outer achromats, such as, of the outer achromats opposite the respective inner achromat.

The holding sleeve can have an outer diameter which corresponds to the outer diameter of an outer achromat, or to the outer diameter of the two outer achromats. This makes it possible for the outer achromats and the holding sleeve arranged between the outer achromats in which one or both inner achromats are accommodated to be arranged sequentially in a system tube, such as of an endoscope.

The lenses of the one inner achromat, or the lenses of the two inner achromats, can be glued, or respectively cemented in the holding sleeve.

When two inner achromats or the two achromats are accommodated or arranged in the holding sleeve, the holding sleeve can have a stop barrier for the two inner achromats in the interior between the inner achromats. Due to the stop barrier in the inner chamber of the holding sleeve, a stop can be provided for the inner achromats that are each introduced from one side, wherein the space between the two inner achromats arranged in the holding sleeve can be constant due to the stop barrier.

An outer achromat, or the outer achromats, can each have a concave lens with a thickness, wherein the thickness of the concave lens of the outer achromat, or the thicknesses of the concave lenses of the outer achromats, is greater by a factor of at least 1.5, such as by a factor of more than 2, than the outer diameter of the outer achromat or the outer achromats. The concave lenses can be configured as biconcave lenses with a negative focal length. The concave lenses of the outer achromats can be arranged on opposite the ends of the holding sleeve, such as in a system tube.

For one end of the holding sleeve that faces an outer achromat, or the two ends of the holding sleeve that each face an outer achromat, can have a flat bearing surface for the lens of the outer achromat facing the end of the holding sleeve in each case, or a bearing surface for the lenses of the respective outer achromats facing the ends of the holding sleeve in each case. Therefore, the lens of the outer achromat, which is arranged opposite the end of the holding sleeve can be in, or can be brought into, contact with the end of the holding sleeve. Such configuration can yield a precise alignment and positioning of the two outer achromats together with the holding sleeve. Moreover, the outer achromats can be prevented from tilting relative to the holding sleeve.

The lens, such as a concave lens, of the outer achromat which faces the holding sleeve, can have a flat, such as peripheral, bearing shoulder, or the lenses, such as a concave lenses, of the outer achromats that each face the holding sleeve, can each have a flat, such as peripheral, bearing shoulder. The lenses of the outer achromats can be connected, or respectively glued to the ends of the holding sleeve, whereby greater stability of the reversal system can be achieved.

The holding sleeve can be glued to an outer achromat, or to the two outer achromats.

A pair having an outer achromat and an inner achromat can be configured symmetrical to a second pair having an outer achromat and an inner achromat.

The outer achromats and the inner achromats can be arranged in a system tube, such as a system tube of the endoscope.

Such object can be furthermore achieved by an endoscope, such as a laparoscope or uroscope, with at least one reversal system, wherein the endoscope is configured with at least one above-described reversal system. To avoid repetition, explicit reference is made to the statements above.

The endoscope can have an endoscope optical system which has a distal objective as well as a proximal image viewing device such as an eyepiece. Moreover, a relay lens system is provided as an image conductor in a tube, such as an endoscope shaft, between the objective and the image viewer which can have a plurality of sequentially arranged reversal systems.

BRIEF DESCRIPTION OF THE DRAWINGS

Further features will become apparent from the description of embodiments together with the claims and the attached drawings. Embodiments can fulfill individual features or a combination of several features.

The embodiments are described below, without restricting the general idea of the invention, based on an exemplary embodiment in reference to the drawing, whereby we expressly refer to the drawing with regard to the disclosure of all details that are not explained in greater detail in the text, in which the.

DETAILED DESCRIPTION

Figure 1:
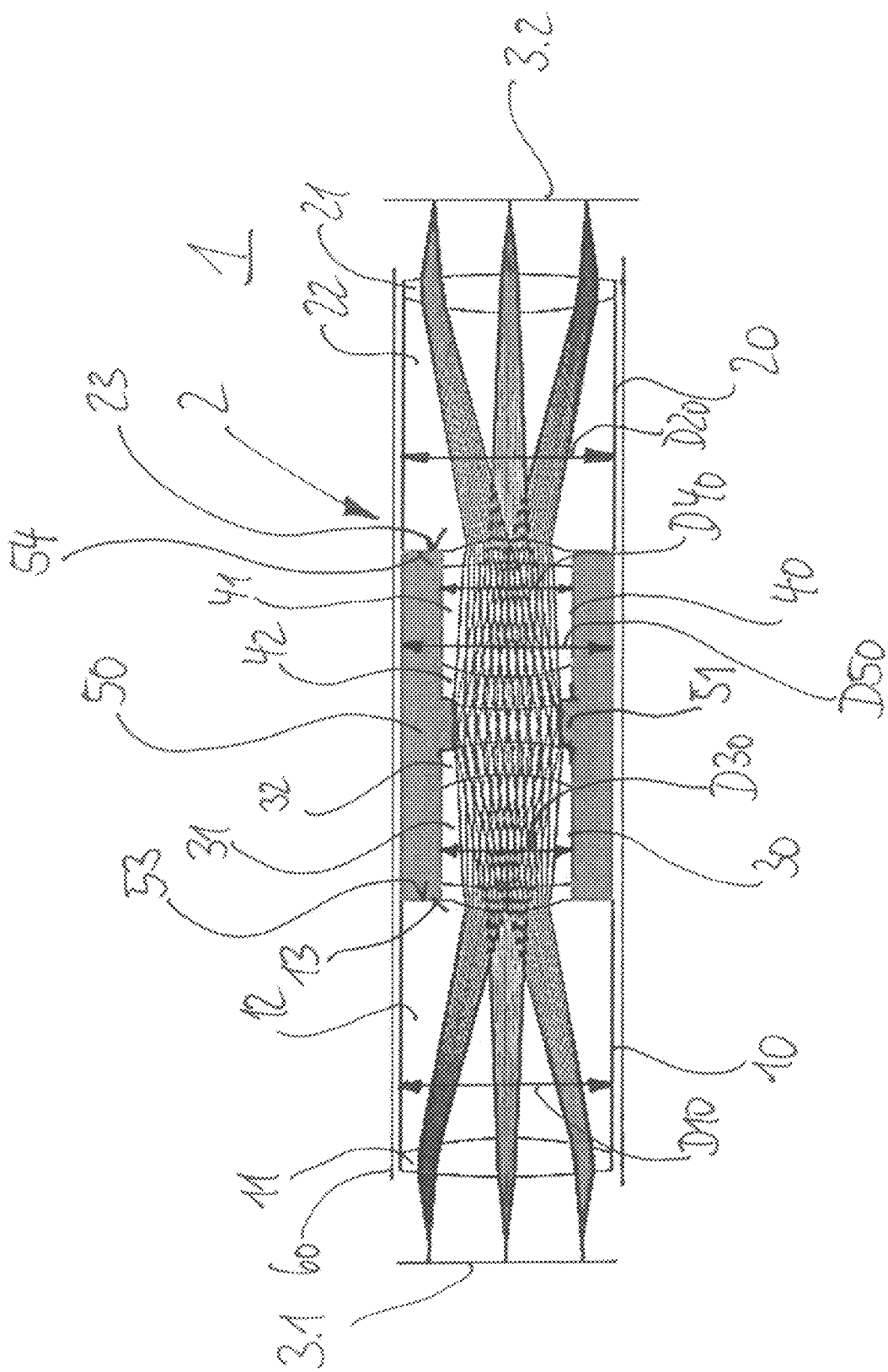
FIG. 1 schematically shows a portrayal of a reversal system for an endoscope.
Figure 2:
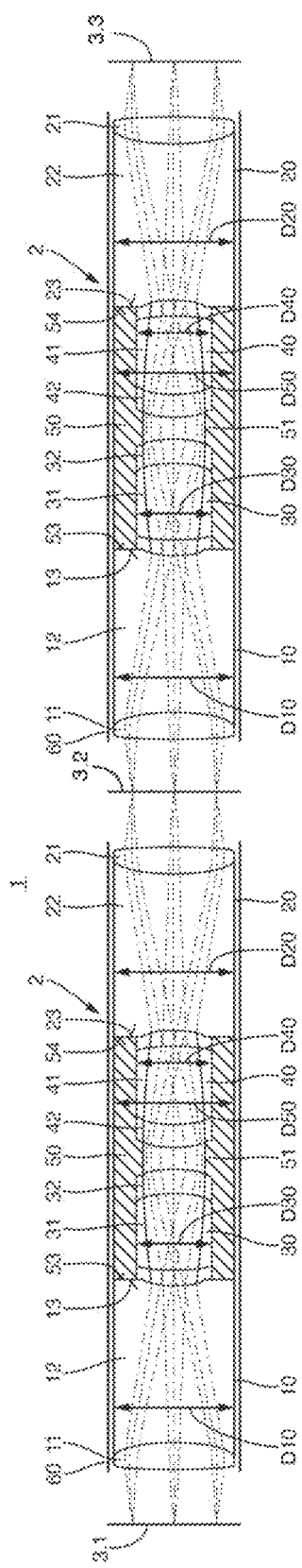
FIG. 2 schematically shows a portrayal of two of the reversal systems of FIG. 1 for an endoscope.

FIG. 1 schematically portrays a reversal system 2 for a schematically identified endoscope 1. The reversal system 2 in this case is a component of an optical system of the endoscope 1. The endoscope 1 can be configured as a rigid endoscope. The optical system of the endoscope 1 can be arranged in a rigid tube (not shown). The optical system of the endoscope 1 can comprise an objective at a distal end, wherein the image generated by the objective is transmitted for example using a plurality of reversal systems, as shown in FIG. 2, to an image plane at the proximal end on which the image is viewed by an eyepiece. A camera can also be arranged on the eyepiece.

The optical system of the endoscope 1 can have a plurality, such as an uneven number, of reversal systems which generate an upright image in the last proximal image plane before the eyepiece.

The reversal system 2 shown in FIG. 1 of the optical system of the endoscope 1 transmits the image from a first image plane 3.1 to a second image plane 3.2. The image, which is present in the image plane 3.1, is shown in reverse on, or respectively in, the image plane 3.2. In so doing, the image of the image plane 3.1 is inverted in the image plane 3.2. The plurality of reversal systems shown in FIG. 2 includes an additional image place 3.3.

The reversal system 2 has two outer achromats 10, 20 between which two inner achromats 30, 40 are arranged. The outer achromat 10 comprises in this case a biconvex lens 11 and a biconcave lens 12. Correspondingly, the outer achromat 20 has a biconvex lens 21 and a biconcave lens 22. The lenses 11, 12 of the outer achromat 10 as well as the lenses 21, 22 of the second outer achromat 20 are in this case configured circular in cross-section, i.e., perpendicular to the plane of the drawing, and have in this case an outer diameter D10, or respectively D20.

The inner achromats 30, 40 arranged between the outer achromats 10, 20 each have a biconvex lens 31, 41, as well as a convex-concave lens 32, or respectively 42.

The lenses 31, 32 of the inner achromat 30 as well as the lenses 41, 42 of the second inner achromat 40 are configured circular in cross-section, and have a diameter D30, or respectively D40. The diameter D30 of the lenses 31, 32 can correspond to the diameter D40 of the lenses 41, 42 of the second inner achromat 40.

The inner achromats 30, 40, or respectively, the lenses 31, 32, 41, 42 of the inner achromats 30, 40 are arranged in a sleeve 50 and accommodated therein. The lenses 31, 32, 41, 42 of the inner achromats 30, 40 can be glued in the sleeve 50. Moreover, a stop barrier 51 that extends radially inward for the lenses 32, 42 is formed in the sleeve 50 between the inner achromats 30, 40. Consequently, the lenses 32, 42 of the achromats 30, 40 are spaced from each other. The sleeve 50 is configured circular in cross-section and has an outer diameter D50. The outer diameter D50 of the sleeve 50 can correspond to the outer diameters D10 and D20 of the outer achromats 10, 20, or respectively their lenses 11, 12, or respectively 21, 22.

The lenses 31, 32 of the achromat 30 as well as the lenses 41, 42 of the achromat 40 are each cemented.

On its ends facing the outer achromats 10, 20, the sleeve 50 has a bearing surface 53, 54. The lenses 12, 22 of the outer achromats 10, 20 are configured elongated, or respectively rod-shaped and (relative to the optical axis) have a length, or respectively thickness that can be greater at least by a factor of 1.5 than the respective outer diameter D10, or respectively D20 of the lens 12, 22, or respectively of the outer achromats 10, 20.

On the sides facing the sleeve 50, the lenses 12, or respectively 22 are configured with a flat shoulder surface 13, or respectively 23 so that the shoulder surfaces 13, or respectively 23 of the lenses 12, 22 are arranged opposite the bearing surfaces 53, 54 of the sleeve and may be connected thereto. In this case, the shoulder surfaces 13, 23 of the lenses 12, 22 are in contact with the bearing surfaces 53, 54 of the sleeve 50.

The outer achromats 10, 20 as well as the inner achromats 30, 40 are arranged in a schematically represented system tube 60 of the endoscope 1 so that the achromats 10, 20, 30, 40 of the system tube 60, such as a fiber tube, are surrounded.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE SIGNS

1 Endoscope
2 Reversal system 3.1, 3.2, 3.3 Image plane
10 Achromat
11 Biconvex lens
12 Biconcave lens
13 Shoulder surface
20 Achromat
21 Biconvex lens
22 Biconcave lens
23 Shoulder surface
30 Inner achromat
31 Biconvex lens
32 Convex-concave lens
40 Inner achromat
41 Biconvex lens
42 Convex-concave lens
50 Sleeve
51 Stop barrier
53 Bearing surface
54 Bearing surface
60 System tube
D10 Outer diameter
D20 Outer diameter
D30 Outer diameter
D40 Outer diameter
D50 Outer diameter

What is claimed is:

1. A reversal system for an endoscope, the reversal system comprising:
    first and second outer achromats each comprising at least two lenses, wherein the first and second outer achromats each have a first outer diameter;
    first and second inner achromats arranged between the first and second outer achromats, wherein each of the first and second inner achromats comprises at least two lenses; and
    a holding sleeve having an interior for accommodating each of the first and second inner achromats,
    wherein the holding sleeve having a second outer diameter equal to the first outer diameter of the first and second outer achromats and the holding sleeve with the first and second inner achromats is arranged between the first and second outer achromats;
    the at least two lenses of the first outer achromat comprises a first concave lens having a first flat shoulder surface contacting a mating first flat bearing surface at a first end of the holding sleeve;
    the at least two lenses of the second outer achromat comprises a second concave lens having a second flat shoulder surface contacting a mating second flat bearing surface at a second end of the holding sleeve.

2. The reversal system according to claim 1, wherein the at least two lenses of the first and second inner achromats are glued in the holding sleeve.

3. The reversal system according to claim 1, wherein the holding sleeve comprising a stop barrier positioned in the interior of the holding sleeve for separating the first and second inner achromats relative to each other.

4. The reversal system according to claim 1, wherein each of the first and second concave lenses having a thickness at least 1.5 times greater than the first outer diameter of the first and second outer achromats.

5. The reversal system according to claim 4, wherein the thickness is at least 2 times greater than the first outer diameter of the first and second outer achromats.

6. The reversal system according to claim 1, wherein the first and second flat shoulder surfaces are peripherally formed.

7. The reversal system according to claim 1, wherein the first flat shoulder surface is glued to the first flat bearing surface and the second flat shoulder surface is glued to the second flat bearing surface.

8. The reversal system according to claim 1, wherein the first and second inner achromats, the first and second outer achromats and the sleeve comprise a reversal assembly, wherein an even number of the reversal assemblies are provided.

9. The reversal system according to claim 1, further comprising a system tube for accommodating the first and second outer achromats, the first and second inner achromats and the sleeve.

10. An endoscope comprising at least one reversal system according to claim 1.

* * * * *